United States Patent
Aasum et al.

(10) Patent No.: US 12,357,006 B2
(45) Date of Patent: Jul. 15, 2025

(54) USE OF ALPHA LIPOIC ACID AS A FEED ADDITIVE FOR AQUATIC ANIMALS

(71) Applicants: DSM IP ASSETS B.V., Te Heerlen (NL); BIOMAR GROUP A/S, Arhus C (NO)

(72) Inventors: Elisabeth Aasum, Kaiseraugst (CH); Ralph Bickerdike, Kaiseraugst (CH); David Christian Martin, Kaiseraugst (CH); Viviane Verlhac, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 1070 days.

(21) Appl. No.: 17/046,097

(22) PCT Filed: Apr. 10, 2019

(86) PCT No.: PCT/EP2019/059166
§ 371 (c)(1),
(2) Date: Oct. 8, 2020

(87) PCT Pub. No.: WO2019/197503
PCT Pub. Date: Oct. 17, 2019

(65) Prior Publication Data
US 2021/0030023 A1 Feb. 4, 2021

(30) Foreign Application Priority Data

Apr. 10, 2018 (CH) .................................. 00456/18

(51) Int. Cl.
| | | |
|---|---|---|
| *A23K 20/158* | (2016.01) | |
| *A23K 20/147* | (2016.01) | |
| *A23K 20/163* | (2016.01) | |
| *A23K 20/174* | (2016.01) | |
| *A23K 40/20* | (2016.01) | |
| *A23K 40/25* | (2016.01) | |
| *A23K 40/30* | (2016.01) | |
| *A23K 50/80* | (2016.01) | |
| *A61K 31/355* | (2006.01) | |
| *A61K 31/415* | (2006.01) | |
| *A61K 47/44* | (2017.01) | |

(52) U.S. Cl.
CPC .......... *A23K 20/158* (2016.05); *A23K 20/147* (2016.05); *A23K 20/163* (2016.05); *A23K 20/174* (2016.05); *A23K 40/20* (2016.05); *A23K 40/25* (2016.05); *A23K 40/30* (2016.05); *A23K 50/80* (2016.05); *A61K 31/355* (2013.01); *A61K 31/415* (2013.01); *A61K 47/44* (2013.01)

(58) Field of Classification Search
CPC .. A23K 20/158; A23K 20/147; A23K 20/163; A23K 20/174; A23K 40/20; A23K 40/25; A23K 40/30; A23K 50/80; A61K 31/355; A61K 31/415; A61K 47/44
See application file for complete search history.

(56) References Cited

U.S. PATENT DOCUMENTS

| | | | | |
|---|---|---|---|---|
| 2011/0229537 A1* | 9/2011 | Matravers | .............. | A61Q 19/00 424/94.1 |
| 2012/0183668 A1* | 7/2012 | Odom | .................... | A23K 40/25 426/601 |
| 2016/0193306 A1* | 7/2016 | Rabovsky | .............. | A61K 36/81 424/93.3 |

FOREIGN PATENT DOCUMENTS

| | | | | |
|---|---|---|---|---|
| CL | 2018000433 | 2/2018 | | |
| CN | 104171594 | 12/2014 | | |
| CN | 105309841 | 2/2016 | | |
| CN | 105705030 | 6/2016 | | |
| JP | 2008-50330 | 3/2008 | | |
| JP | 2013-188207 | 9/2013 | | |
| KR | 10-0811110 | 3/2008 | | |
| WO | 01/67896 | 9/2001 | | |
| WO | 2008/097103 | 8/2008 | | |
| WO | WO-2009039716 A1 * | 4/2009 | ............. | A23D 9/007 |
| WO | 2015/011644 | 1/2015 | | |
| WO | WO 2017/0029558 | 2/2017 | | |

OTHER PUBLICATIONS

Shi Xiao-Chen et al., Fish and Shellfish Immunology, Academic Press, London, GB, vol. 67, Jun. 14, 2017 (Jun. 13, 2017), pp. 359-367, XP085129824, ISSN: 1050-4648. (Year: 2017).*
Shi et al. a-lipoic acid ameliorates n-3 highly-unsaturated fatty acids induced lipid peroxidation via regulating antioxidant defenses in grass carp (*Ctenopharyngodon idellus*), in Fish & Shellfish Immunology, 2017, pp. 359-367. (Year: 2017).*
Powder Technology Inc. (https://www.powdertechnologyinc.com > particle-size-an . . . ), Mar. 13, 2011. (Year: 2011).*
Kutter et al. "Effects of Dietary-lipoic acid on growth, body composition and antioxidant status in the Plata pompano Trachinotus marginatus (Pisces, Carangidae)" in Aquaculture, 368-369 (2012) 29-35. (Year: 2012).*

(Continued)

*Primary Examiner* — Blessing M Fubara
(74) *Attorney, Agent, or Firm* — Nixon & Vanderhye, P.C.

(57) ABSTRACT

The present invention relates to the use of alpha lipoic acid as feed additive for aquatic animals including fish and shrimp, especially for cold water fish as for example salmon, bream, bass and for warm water fish as for example carp, tilapia, catfish. More particular, this invention relates to the use of alpha lipoic acid for the improvement of the feed conversion ratio and/or daily weight gain in fish, for reducing mortality by regulating the micro flora of the gut and/or by protecting the animal against infections caused by pathogenic viruses.

11 Claims, 7 Drawing Sheets

(56) References Cited

OTHER PUBLICATIONS

International Search Report for PCT/EP2019/059166 mailed Jun. 3, 2019, 4 pages.
Written Opinion of the ISA for PCT/EP2019/059166 mailed Jun. 3, 2019, 9 pages.
Shi et al., "[alpha]-lipoic acid ameliorates n-3 highly-unsaturated fatty acids induced lipid peroxidation via regulating antioxidant defenses in grass carp (*Ctenopharyngodon idellus*)", Fish and Shellfish Immunology, vol. 67, Jun. 13, 2017, pp. 359-367.
Database WPI Week 201630, Thomson Scientific, XP002791526 & CN105309841, Feb. 10, 2016—Abstract, 2 pages.
Database WPI Week 201365, Thomson Scientific, XP002791527 & JP2013188207, Sep. 26, 2015—Abstract, 2 pages.
Database WPI Week 200882, Thomson Scientific, XP002791528 & KR100811110, Mar. 6, 2008—Abstract, 2 pages.
Longaray-Garcia et al., "Modulation of antioxidant and detoxifying capacity in fish Cyprinus carpio (*Cyprinidae*) after treatment with nanocapsules containing lipoic acid", Comparative Biochemistry and Physiology, Part A, Molecular and Integrative Physiology, vol. 165, No. 4, Feb. 9, 2013, pp. 468-475.
Kutter et al., "Effects of dietary a-lipoic acid on growth, body composition and antioxidant status in the Plata pompano *Trachinotus marginatus* (Pisces, Carangidae)", Aquaculture, Jun. 12, 2012, 8 pages.
Zhang et al., "Effects of α-lipoic acid on the growth and antioxidative responses of juvenile abalone Haliotis discus hannai Ino", Aquaculture Research, vol. 41, 2010, pp. 781-787.
BR Appln 202002596, Informe De Búsqueda Sobre Solicitud de Patente de Invención, Nov. 29, 2021.

\* cited by examiner

USE OF ALPHA LIPOIC ACID AS A FEED ADDITIVE FOR AQUATIC ANIMALS

This application is the U.S. national phase of International Application No. PCT/EP2019/059166 filed Apr. 10, 2019 which designated the U.S. and claims priority to CH Patent Application No. 00456/18 filed Apr. 10, 2018, the entire contents of each of which are hereby incorporated by reference.

BACKGROUND OF THE INVENTION

One important factor in aquaculture is the turnover rate. The turnover rate is determined by how fast the fish grow to a harvestable size.

As an example, it takes from 12 to 18 months to raise Atlantic salmon from smolt (the physiological stage when the Atlantic salmon can first be transferred from fresh water to sea water) to harvestable size. A fast turnover has several positive results. First, it helps cash flow. Second, it improves risk management.

The turnover rate may e.g. be affected by the Feed Conversion Rate (FCR) however, it may also be affected by mortality.

It is generally known in the art that the mortality rate increases by an unbalanced microflora and/or by infections caused by pathogenic microbes or viruses. Fish diseases are common, and the likelihood of an outbreak is higher over a long growing period. There is also a risk that fish will escape due to accidents, e.g. when shifting nets, or due to bad weather causing wrecked fish pens.

For other farmed animals it is well known to use antibiotics and vaccines to prevent the development of diseases. In aquaculture, medicated feed with antibiotics are not applied very frequently due to the fact that diseases spread very quickly and that diseased fish have reduced appetite. Also, the surplus of medicated feed not eaten by the fish may have a negative impact on the aquatic environment. Vaccines are widely used, when available, but they are not developed for all diseases. Furthermore, it has been observed that the use of medication and stress very often results in a negative impact on fish performance.

It therefore remains a need in aquaculture industry to prevent the development of diseases, thereby reducing mortality by any prophylactic means including antimicrobial and/or anti-viral activity at the gut level and to restore, even better, to improve performance.

SUMMARY OF THE INVENTION

The inventors of the present application surprisingly found that alpha lipoic acid has a great potential for use in fish feed, e.g. for improving the feed conversion ratio (FCR) and/or weight gain and/or for modulation of the gut flora. Further, the inventors surprisingly found that alpha lipoic acid also has antiviral activity against pancreatic disease virus resulting in a reduced mortality.

Therefore, in one aspect, the present invention relates to a composition comprising as active ingredient alpha-lipoic acid, a salt or derivative thereof, wherein the composition is selected from the group consisting of a feed additive, a feed premix or aquaculture feed, wherein the concentration of the active ingredient in the aquaculture feed is in the range from 150 mg-1000 mg per kg feed.

In a further aspect, the present invention relates to a method of preparing a feed pellet, said method comprising the steps of:

i) combining feed ingredients ii) forming a fish feed pellets comprising said feed ingredients, (iii) obtaining a feed pellet, (iv) coating said pellet with or in an oil comprising alpha-lipoic acid, a salt or derivative thereof and (v) obtaining a feed pellet comprising alpha-lipoic acid or a derivative or a salt thereof in a concentration of between 150 mg and 1000 mg per kg of feed.

In a third aspect, the present invention pertains to the use of alpha-lipoic acid, a salt or derivative thereof for
improving feed conversion ratio and/or daily weight gain (standard growth rate) in aquatic animals; or
reducing mortality in aquatic animals; or
for the treatment and prevention of diseases caused by pathogenic microorganisms or viruses in aquatic animals.

In a fourth aspect, the invention relates to methods for
improving the feed conversion ratio and/or the standard growth rate in aquatic animals; or
for reducing mortality in aquatic animals, or
for the treatment and/or prevention of diseases caused by pathogenic microorganisms or viruses in aquatic animals;
said methods comprise feeding to the aquatic animal a feed comprising alpha-lipoic acid, a salt or derivative thereof.

In a fifth aspect, the present invention pertains to a composition comprising alpha-lipoic acid, a salt or derivative thereof for use in
improving the feed conversion ratio and/or the standard growth rate in aquatic animals; or
in reducing mortality in aquatic animals; or
in the treatment and/or prevention of diseases caused by pathogenic microorganisms or viruses in aquatic animals.

In a further aspect, the present invention pertains to a feed additive composition comprising alpha-lipoic acid, a salt or derivative thereof in the form of a powder with a particle size below 1 mm, optionally embedded in an oil carrier.

In a further aspect, the present invention pertains to a premix composition or aquaculture feed additive comprising alpha-lipoic acid, a salt or derivative thereof and at least one additional component selected from the group consisting of fat-soluble vitamins, water soluble vitamins, carotenoids, polyunsaturated fatty acids, trace minerals, probiotics, prebiotics and macro minerals.

DEFINITIONS

Figure 1:
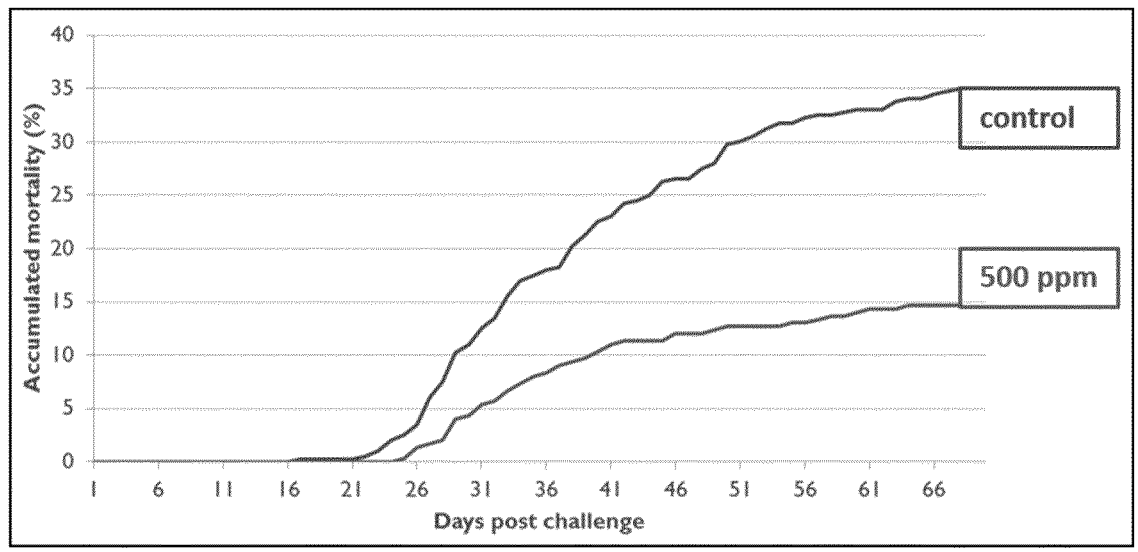
FIG. 1. Accumulated mortality in Atlantic salmon fry following SAV challenge comparing fish fed control diet or a feed comprising 500 mg alpha-lipolic acid/kg feed.

Aquatic Animal: The term "aquatic animal" refers to crustaceans including but not limited to shrimps and prawns and fish including but not limited to amberjack, arapaima, barb, bass, bluefish, bocachico, bream, bullhead, cachama, carp, catfish, catla, chanos, char, cichlid, cobia, cod, crappie, dorada, drum, eel, goby, goldfish, gourami, grouper, guapote, halibut, java, labeo, lai, loach, mackerel, milkfish, mojarra, mudfish, mullet, paco, pearlspot, pejerrey, perch, pike, pompano, roach, salmon, sampa, sauger, sea bass, seabream, shiner, sleeper, snakehead, snapper, snook, sole, spinefoot, sturgeon, sunfish, sweetfish, tench, terror, tilapia, trout, tuna, turbot, vendace, walleye and whitefish.

Feed Additive: The term feed additive according to the invention refers to a formulation comprising alpha-lipoic acid as active ingredient intended for intake by the fish.

Feed Premix: The incorporation of the composition of feed additives as exemplified herein above to animal feeds, for example fish feeds, is in practice carried out using a concentrate or a premix. A premix designates a preferably uniform mixture of one or more microingredients with diluent and/or carrier. Premixes are used to facilitate uniform dispersion of micro-ingredients in a larger mix. A premix according to the invention can be added to feed ingredients as solids (for example as water soluble powder) or liquids.

Feed or Aquaculture feed: The term "Feed" or "Aquaculture feed" or "aquatic feed" refers to any compound, preparation, or mixture suitable for, or intended for intake by aquatic animals and decapod crustacean. An animal feed for aquatic animals typically comprises high protein and energy concentrations, such as fish meal, molasses, oligosaccharide concentrates as well as vitamins, minerals, enzymes, direct fed microbial, amino acids and/or other feed ingredients (such as in a premix). Aquaculture feed refers to a manufactured or artificial diet (i.e., formulated feed) to supplement or to replace natural feed, which is most commonly produced in form of flakes or pellets. Preferred embodiment of feed pellets are characterized by a pellet size (diameter) in a range from 0.5 to 16 mm pellet size (diameter) roughly and a protein-content from 20% to 65% w/w.

Typically, a decapod crustacean feed may be in the form of flakes or pellets, for example extruded pellets. In the present context the term "decapod crustacean feed " may e.g. be a shrimp or prawn feed.

Feed efficiency: The term "feed efficiency" means the amount of weight gain per unit of feed when the animal is fed ad-libitum or a specified amount of food during a period of time. By "increased feed efficiency" it is meant that the use of a feed additive composition according the present invention in feed results in an increased weight gain per unit of feed intake compared with an animal fed without said feed additive composition being present.

Feed Conversion Ratio (FCR): FCR is a measure of an animal's efficiency in converting feed mass into increases of the desired output. Animals raised for meat—such as swine, poultry and fish—the output is the mass gained by the animal. Specifically, FCR is calculated as feed intake divided by weight gain, all over a specified period. Improvement in FCR means reduction of the FCR value. An FCR improvement of 2% means that the FCR was reduced by 2%.

Specific Growth Rate (SGR): The term Specific Growth Rate (SGR) according to the invention refers to the daily increase in bodyweight (in %).

DETAILED DESCRIPTION OF THE INVENTION

The present invention relates to the use of alpha lipoic acid as feed additive for aquatic animals including fish and decapod crustaceans.

More particular, this invention relates to the use of alpha lipoic acid, a salt or derivative thereof for the improvement of the feed conversion ratio and/or daily weight gain in fish, for reducing mortality by regulating the micro flora of the gut and/or by protecting the animal against infections caused by pathogenic viruses.

Furthermore, the present invention relates to a novel aquatic feed composition comprising as active ingredient alpha lipoic acid, a salt or derivative thereof, wherein the composition is selected from the group consisting of a feed additive, a feed premix or aquaculture feed.

There is prior art on lipoic acid in connection with anti-viral activities, inducing apoptosis in proliferating cancer cells, and also inhibiting apoptosis including reducing cardiomycytes apoptosis in higher vertebrates, however nothing is disclosed on the use in aquaculture for improving feed conversion ratios (FCR) or the the treatment and/or prevention of diseases caused by pathogenic microorganisms or viruses in aquatic animals through lipoic acid.

In a first particular embodiment, the invention relates to methods for using alpha lipoic acid for improving Standard Growth Rate (SGR) and Feed Conversion Ratio (FCR) in aquatic animals and/or weight gain in aquatic animals and/or for reducing mortality in aquatic animals by modulation of the gut microflora.

The FCR may be determined on the basis of a growth trial comprising a first treatment in which a mixture of at least two compounds according to the invention is added to the animal feed in a suitable concentration per kg feed, and a second treatment (control) with no addition of the compound (s) to the animal feed.

As it is generally known, an improved FCR is lower than the control FCR. In particular embodiments, the FCR is improved (i.e., reduced) as compared to the control by at least 1.0%, preferably at least 1.5%, 1.6%, 1.7%, 1.8%, 1.9%, 2.0%, 2.1%, 2.2%, 2.3%, 2.4% or at least 2.5%.

The term "gut" as used herein designates the gastrointestinal or digestive tract (also referred to as the alimentary canal) and it refers to the system of organs within multicellular animals which takes in food, digests it to extract energy and nutrients, and expels the remaining waste.

The term gut "microflora" as used herein refers to the natural microbial cultures residing in the gut and maintaining health by aiding in proper digestion.

The term "modulate" as used herein in connection with the gut microflora generally means to change, manipulate, alter, or adjust the function or status thereof in a healthy and normally functioning animal, i.e. a non-therapeutic use.

The term "mortality" as used herein refers to the ratio of life animals at the end of the growth phase in the pond versus the number of animals originally included into the pond. It may be determined on the basis of a fish challenge trial comprising two groups of fish challenged by a particular fish pathogen with the aim to provoke a mortality of 40 to 80% of the animals in the untreated group. However, in the challenge group fed with a suitable concentration per Kg of feed of a mixture of at least two compounds one being alpha-lipolic acid, a salt or derivative thereof, the mortality is reduced compared to the untreated group by at least 5%, preferably at least, 10%, 15%,20%, 25%, 30%, 35%, 40%, 45%, or at least 50%.

In particular, the inventors of the present application surprisingly found that the one being alpha-lipolic acid, a salt or derivative thereof is effective against infections caused by pathogenic microbes or viruses.

In one embodiment of the present invention the aquatic animal disease is selected from the group consisting of pancreatic disease (PD), white spot disease, cardiomyopathy syndrome (CMS) and skeletal muscle inflammation (HSMI).

In one embodiment the virus may be an alpha virus. The alpha virus may be salmonid alphavirus subtype 2 (SAV-2) virus and/or salmonid alphavirus subtype 3 (SAV-3) virus which can cause pancreatic disease.

In a further embodiment the virus may be mycocardits virus (PMCV) which is a totivirus of the Totiviridae family. In yet an embodiment the virus may be piscine reovirus (PRV) which is a retrovirus of the Reoviridae family).

In an embodiment the virus may be a nodavirus of the family Nodaviridae. More specifically the nodavirus may be selected from the group consisting of piscine nodavirus, white spot syndrome virus, *Macrobrachium rosenbergii* nodavirus (MrNV) and *Penaeus vannamei* nodavirus (PvNV).

Therefore, in a second particular embodiment, the invention relates to methods for using alpha lipoic acid for preventing or treating diseases caused by microbial or viral infections.

In a third particular embodiment, the invention relates to a composition comprising as active ingredient alpha-lipoic acid, a salt or derivative thereof for use in
- improving the feed conversion ratio and/or the standard growth rate in aquatic animals;
- reducing mortality in aquatic animals;
- in the treatment and/or prevention of diseases caused by pathogenic microorganisms or viruses in aquatic animals.

A feed additive composition according to the invention can be made as described in example 3. The active ingredient of such a composition can be alpha lipoic acid, a salt or derivative thereof. The alpha lipoic acid, a salt or derivative thereof is sieved to achieve a particle size below 1 mm and embedded in an oil carrier.

Said oil carrier can be fish oil, microbial oil and/or one or more vegetable oil(s). The vegetable oil can be selected from the group consisting of rape seed oil and soy oil. An example of a microbial oil according to the invention is an oil from *Schizochytrium*. Preferably, the oil is a source of eicosapentaenoic acid ("EPA") and/or docosahexaenoic acid ("DHA"). "Eicosapentaenoic acid" ["EPA"] is the common name for eis-5, 8, 11,14, 17-eicosapentaenoic acid. This fatty acid is a 20:5 omega-3 fatty acid. "Docosahexaenoic acid" ["DHA"] is the common name for eis-4, 7, 10, 13, 16, 19-docosahexaenoic acid. This fatty acid is a 22:6 omega-3 fatty acid.

Alpha lipoic acid is commercially available, for example from SUZHOU FUSHILAI PHARMACEUTICALCO., LTD., as a crystalline powder in high purity.

The incorporation of the feed additive composition containing the alpha lipoic acid, a salt or derivative thereof into fish feed may be performed as described in example 1 and 2. The final concentration of alpha lipoic acid in the feed is determined by HPLC according to standard methods.

The incorporation of the feed additive composition containing the alpha lipoic acid, a salt or derivative thereof into fish feed may alternatively be carried out by preparing a premix of the alpha lipoic acid, a salt or derivative thereof and other suitable additives. Such a premix may comprise 2-10% by weight of the alpha lipoic acid, a salt or derivative thereof, 0-40% by weight of other conventional additives, such as flavorings, and 50-98% by weight of any conventional absorbing support.

The support may contain, for example, 40-50% by weight of wood fibers, 8-10% by weight of stearin, 4-5% by weight of curcuma powder, 4-5% by weight of rosemary powder, 22-28% by weight of limestone, 1-3% by weight of a gum, such as gum Arabic, 5-50% by weight of sugar and/or starch and 5-15% by weight of water.

The premix may also contain vitamins, as for example vitamin E, mineral salts and other feed additive ingredients, as for example yeast extracts containing nucleotides, glucan and other gut microflora modulators such as pro- and/or prebiotics and then finally added to the feed in such quantities that the feed comprises 10-5000 ppm, preferably 100-1000 ppm, 150-1000ppm, 500-1000, 500-750 or 100-500 ppm of alpha lipoic acid, a salt or derivative thereof on.

Further, optional, feed-additive ingredients which can be added to the premix are coloring agents, e.g. carotenoids such as beta-carotene, astaxanthin, and lutein; aroma compounds; stabilisers; antimicrobial peptides; polyunsaturated fatty acids; and/or at least one enzyme selected from amongst phytase (EC 3.1.3.8 or 3.1.3.26); xylanase (EC 3.2.1.8); galactanase (EC 3.2.1.89); alpha-galactosidase (EC 3.2.1.22); protease (EC 3.4.), phospholipase A1 (EC 3.1.1.32); phospholipase A2 (EC 3.1.1.4); lysophospholipase (EC 3.1.1.5); phospholipase C (EC 3.1.4.3); phospholipase D (EC 3.1.4.4); amylase such as, for example, alpha-amylase (EC 3.2.1.1); and/or beta-glucanase (EC 3.2.1.4 or EC 3.2.1.6).

Examples of polyunsaturated fatty acids are C18, C20 and C22 polyunsaturated fatty acids, such as arachidonic acid, docosohexaenoic acid, eicosapentaenoic acid and gamma-linoleic acid. Fish oil, microbial oil and/or one or more vegetable oil(s) are sources of these fatty acids. The vegetable oil can be selected from the group consisting of rape seed oil and soy oil. An example of a microbial oil according to the invention is an oil from *Schizochytrium*.

A preferred premix composition according to the invention comprises as active ingredient alpha-lipoic acid, a salt or derivative thereof and a vitamin E preparation wherein the fat soluble vitamin E preparation is at least one compound selected from the group consisting of alpha-tocopherol, beta-tocopherol, gamma-tocopherol, delta-tocopherol, alpha-tocotrienol, beta-tocotrienol, gamma-tocotrienol, delta-tocotrienol and their esters, preferably their acetates. Such a premix has the advantage that the presence of Vitamin E stabilizes the active ingredient.

Another preferred premix composition according to the invention comprises as active ingredient alpha-lipoic acid, a salt or derivative thereof and a coating oil in which the active ingredient is dissolved or suspended.

Said coating oil can be fish oil, microbial oil and/or one or more vegetable oil(s). The vegetable oil can be selected from the group consisting of rape seed oil and soy oil. An example of a microbial oil according to the invention is an oil from *Schizochytrium*. Preferably, the oil is a source of eicosapentaenoic acid ("EPA") and/or docosahexaenoic acid ("DHA").

In another embodiment, the invention relates to a feed or fish feed composition for aquatic animals.

The term "feed" or "fish feed" or "aquatic feed" as used herein includes a fish feed composition according to the invention and components as described above. Typically, fish feed includes fish meal as a component. Suitably, fish feed is in the form of flakes or pellets, for example extruded pellets.

In one embodiment the feed comprises from 150 mg alpha lipoic acid, a salt or derivative thereof per kg feed, such as in the range from 200-450 mg alpha lipoic acid, a salt or derivative thereof per kg feed, e.g. in the range from 250-400 mg alpha lipoic acid, a salt or derivative thereof per kg feed, such as in the range from 300-350 mg alpha lipoic acid, a salt or derivative thereof per kg feed.

In one embodiment the feed comprises from 200 mg alpha lipoic acid, a salt or derivative thereof per kg feed, preferably from 250, 300, 350, 400, 450, 500, 550, 600, 650, 700, 750, 800, 850, 900, 950, 1000 mg per kg feed.

In one embodiment the feed comprises up to 1000 mg alpha lipoic acid, a salt or derivative thereof per kg feed, preferably up to 950, 900, 850, 7800, 750, 700, 650, 600, 550, 500, 450, 400, 350, 300, 250 mg per kg feed.

In one embodiment the feed comprises alpha lipoic acid, a salt or derivative thereof in the range from 150-1000 mg per kg feed, preferably in the range from 200-950, 250-900, 300-850, 350-800, 400-750, 450-700, 500-650 mg per kg feed.

In one specific embodiment the aquatic animal feed thereof per kg feed, such as in the range from 200-1000 mg alpha lipoic acid, a salt or derivative thereof per kg feed, e.g. in the range from 250-950 mg alpha lipoic acid, a salt or derivative thereof per kg feed, such as in the range from 300-900 mg alpha lipoic acid, a salt or derivative thereof per kg feed, e.g. in the range from 400-850 mg alpha lipoic acid, a salt or derivative thereof per kg feed, such as in the range from 450-800 mg alpha lipoic acid, a salt or derivative thereof per kg feed, e.g. in the range from 500-750 mg alpha lipoic acid, a salt or derivative thereof per kg feed, such as in the range from 550-700 mg alpha lipoic acid, a salt or derivative thereof per kg feed, e.g. in the range from 600-650 mg alpha lipoic acid, a salt or derivative thereof per kg feed, such as preferably in the range from 250-1000 mg alpha lipoic acid, a salt or derivative thereof per kg feed.

The fish feed as described herein comprises a proximate composition of 20-60 wt.-% protein, and 1-45 wt.-% moisture and lipid.

In one embodiment the aquatic animal feed is a fish feed or a decapod crustacean feed.

In some specific examples, the aquatic feed comprises one or more of sources of:
protein, carbohydrate and lipid (for example, fish meal, fish oil, blood meal, feather meal, poultry meal, chicken meal and/or other types of meal produced from other slaughterhouse waste),
animal fat (for example poultry oil),
vegetable meal (e.g. soya meal, lupin meal, pea meal, bean meal, rape meal and/or sunflower meal),
vegetable oil (e.g. rapeseed oil, soya oil and/or camelina oil),
gluten (e.g. wheat gluten or corn gluten) and added amino acids (e.g. lysine)
ash
moisture such as e.g. water.

Thus, in one embodiment the aquatic animal feed of the present invention may comprise ingredients selected from the group consisting of a carbohydrate source, a protein source, a lipid source, ash, water and any combinations thereof.

Typically, the protein source may constitute from 20-60% (w/w) of the composition and/or fish feed, such as from 26-54% (w/w), e.g. from 27-53% (w/w), such as from 28-52% (w/w), e.g. from 27-51% (w/w), such as from 28-50% (w/w), e.g. from 29-49% (w/w), such as from 30-48% (w/w), e.g. from 31-47% (w/w), such as from 32-46% (w/w), e.g. from 33-45% (w/w), such as from 34-44% (w/w), e.g. from 35-43% (w/w), such as from 36-42% (w/w), such as from 37-41% (w/w), e.g. from 38-40% (w/w), such as from 39-40% (w/w), e.g. from 20-40% (w/w), such as from 25-60% (w/w), preferably in the range from 30-55% w/w.

The carbohydrate source may constitute from 10-25% (w/w) of the composition and/or fish feed, such as from 11-24% (w/w), e.g. from 12-23% (w/w), such as from 13-24% (w/w), e.g. from 14-23% (w/w), such as from 15-24% (w/w), e.g. from 16-23% (w/w), such as from 17-22% (w/w), e.g. from 18-21% (w/w), such as from 19-20% (w/w), preferably in the range from 10-15% (w/w).

The lipid source may constitute from 15-40% (w/w) of the composition and/or fish feed, such as from 16-39% (w/w), e.g. from 17-38% (w/w), e.g. 18-37% (w/w), such as from 19-36% (w/w), e.g. from 20-35% (w/w), such as from 21-36% (w/w), e.g. from 22-35% (w/w), such as from 23-36% (w/w), e.g. from 24-35% (w/w), such as from 25-34% (w/w), e.g. from 26-33%, such as from 27-32% (w/w), e.g. from 28-33%, such as from 29-32% (w/w), e.g. from 30-31% preferably in the range from 25-40% (w/w).

In a further embodiment, the invention relates to a method of providing an extruded feed pellet, said method comprising the steps of claim 18.

Feed pellets (such as aquatic feed pellets) according to the present invention may be extruded pellets. The extruded feed pellets may be produced by the method of the present invention.

In preferred examples the final feed pellets comprises 1 to 40%, for example 12 to 45% coating oil according to the invention.

It may be contemplated that the extruded feed pellet(s) has a DORIS value in the range from 75-100%. The DORIS value is measured on a DORIS tester (Durability on a Realistic Test) (Akvasmart, AKVA group ASA, Bryne, Norway). The DORIS tester is designed to mimic the pellet degradation during pneumatic feeding system. The result is between 0% and 100%, and corresponds to the mass fraction (m/m) of whole pellets after DORIS exposure relative to the initial sample mass.

It may also be contemplated that the extruded feed pellets of the present invention has a pellet hardness in the range from 20-100N. The pellet hardness is determinded on a pellet strength texture analyzer from Stable Micro Systems Ltd, Godalming, More specifically a TA-XT plus Texture Analyzer (TA) from Stable Micro Systems mounted with a cylindrical probe (P/40) was used to determine pellet hardness.

The feed can be fed to all types of fish, including cold-water fish and shrimp. Some examples are turbot, halibut, yellow tail salmon, trout, bream, bass and tuna. The feed is particularly suitable for feeding salmonids, including Atlantic salmon (*Salmo salar*), other salmon species and trout, and non-salmonids such as cod, sea bass, sea bream and eel. It is suitable for feeding salmon, trout, bream and/or bass in the fresh water (FW) phase and the in the sea water (SW) phase and in the period after hatching and until slaughter and in all stages, such as fry, fingerlings, parr, smolts and adult fish.

The composition of the present invention (i.e. a feed, a feed additive, a premix and an oil) may be particularly suitable for aquatic animals and for a variety of aquatic animal species.

In a particular preferred embodiment of the present invention, the aquatic animal is a fish or a decapod crustacean.

The fish may be any kind of fish such as but not limited to a fish selected from the group consisting of salmon, trout, sea bream, sea bass, cod, eel, turbot, halibut, yellow tail, tuna, carp, tilapia and catfish. In a particular preferred embodiment, the fish is selected from the group consisting of salmon, trout, sea bream and sea bass.

The salmon may be of the family Salmonidae and of the subfamily of Salmoninae. In one embodiment the salmon is selected from the group consisting of the genus *Salmo, Oncorhynchus* and *Salvenis*. In a further embodiment the genus *Salmo* is selected from the group consisting of Atlantic salmon (*Salmo salar*) and Brown trout (*Salmo trutta*). In yet an embodiment the genus *Oncorhynchus* is selected from the group consisting of Chinook salmon (*Oncorhynchus tshawytsch*), Rainbow trout (*Oncorhynchus mykiss*), Sockeye salmon (*Oncorhynchus nerka*) and Coho salmon (*Oncorhynchus kisutch*). In a further embodiment the genus *Salvenis* is selected from the group consisting of Arctic charr (*Salvelinus alpinus*), Brook trout (*Salvelinus fontinalis*) and Lake trout (*Salvelinus namaycush*).

The sea bream may be gilt-head sea bream (*Sparus aurata*) wheras the sea bass may be European bass (*Dicentrarchus labrax*)

In a preferred embodiment of the present invention the decapod crustacean may be shrimp or prawn.

The shrimp may be selected from the group consisting of Pacific white shrimp (*Penaeus vannamei* or *Litopenaeus vannamei*), Whiteleg shrimp (*Penaeus vannamei* or *Litopenaeus vannamei*), Black tiger shrimp (*Penaeus monodon*), Kuruma shrimp (*Penaeus japonicas* or *Marsupenaeus japonicas*), Western blue shrimp (*Penaeus stylirostris* or *Litopenaeus stylirostris*), blue shrimp (*Penaeus stylirostris* or *Litopenaeus stylirostris*), Chinese white shrimp (*Penaeus chinensis* or *Fenneropenaeus chinensis*), Oriental shrimp (*Penaeus chinensis* or *Fenneropenaeus chinensis*), Indian white shrimp (*Penaeus indicus* or *Fenneropenaeus indicus*), Banana shrimp (*Penaeus merguiensis* or *Fenneropenaeus merguiensis*), Akiami paste shrimp (*Metapenaeus* spp.), yellowleg shrimp (*Penaeus californiensis* or *Farfantepenaeus californiensis*), brown shrimp (*Penaeus californiensis* or *Farfantepenaeus californiensis*), São Paulo shrimp (*Penaeus paulensis* or *Farfantepenaeus paulensis*), Carpas shrimp (*Penaeus paulensis* or *Farfantepenaeus paulensis*), redspotted shrimp (*Penaeus brasiliensis* or *Farfantepenaeus brasiliensis*), spotted pink shrimp (*Penaeus brasiliensis* or *Farfantepenaeus brasiliensis*)and southern white shrimp (*Penaeus schmitti*).

The prawn may be selected from the group consisting of King prawn (*Penaeus vannamei* or *Litopenaeus vannamei*), Giant tiger prawn (*Penaeus monodon*), Giant Freshwater Prawn (*Macrobrachium rosenbergii*), Giant river prawn (*Macrobrachium rosenbergii*), Malaysian prawn (*Macrobrachium rosenbergii*), Kuruma prawn (*Penaeus japonicas* or *Marsupenaeus japonicas*), Fleshy prawn (*Penaeus chinensis* or *Fenneropenaeus chinensis*), Indian prawn (*Penaeus indicus* or *Fenneropenaeus indicus*), Banana prawn (*Penaeus merguiensis* or *Fenneropenaeus merguiensis*), Oriental river prawn (*Macrobrachium nipponense*) and Monsoon river prawn (*Macrobrachium malcolmsonii*).

The composition of the present invention may be administered (i.e. fed) to the aquatic animal in the period after hatching and until slaughter. This also means that the composition may be administered (i.e. fed) the aquatic animal in fresh water (FW) or in sea water (SW) dependent on the life stage of the aquatic animal.

In respect of fish the composition of the present invention may be administered (i.e. fed) to the fish during all life stages and thus, the fish may be selected from the group consisting of larvae, fry, fingerlings, parr, smolts and adult fish.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Embodiments of the Invention can be Summarized as Follows

1. A composition comprising as an active ingredient alpha-lipoic acid, a salt or derivative thereof, wherein the composition is intended for intake by aquatic animals and wherein and the concentration of the active ingredient in the final feed added to the animal is in the range from 150 mg-1000 mg per kg feed.

2. The composition according to claim 1, wherein the composition is a feed additive comprising the active ingredient in the form of a powder with a particle size below 1 mm.

3. The composition according to claim 2, wherein the active ingredient is embedded in an oil carrier.

4. The composition according to claim 1, wherein said composition is a feed premix, wherein said premix comprises in addition to the active ingredient at least one additional component selected from the group consisting of fat-soluble vitamins, water soluble vitamins, trace minerals, carotenoids, polyunsaturated fatty acids, probiotics, prebiotics and macro minerals.

5. The composition according to claim 4, wherein the fat-soluble vitamin is vitamin E.

6. The composition according to claim 4 or 5, wherein the fat-soluble vitamin is at least one compound selected from the group consisting of alpha-tocopherol, beta-tocopherol, gamma-tocopherol, delta-tocopherol, alpha-tocotrienol, beta-tocotrienol, gamma-tocotrienol, delta-tocotrienol and their esters, preferably their acetates.

7. The composition according to claim 3 to 6, comprising a coating oil, wherein said coating oil is selected from the group consisting of fish oil, microbial oil and/or one or more vegetable oil(s).

8. The composition according to claim 7, wherein said coating oil comprises oleic acid (18:1n-9) in the range 0.28-229.15 g/kg feed, linoleic acid in the range 0.22-233.24 g/kg feed, alfa-linolenic acid in the range 0.28-225.06 g/kg, arachidonic acid (ARA, 20:4 n-6) in the range 0.03-24.55 g/kg, eicosapentaenoic acid (EPA, 20:5 n-3) in the range 0.03-73.66 g/kg and docosahexaenoic acid (DHA, 22:6 n-3) in the range 0.03-73.66 g/kg.

9. The composition according to claim 8, wherein the vegetable oil is selected from the group consisting of rape seed oil, soy oil and camelina oil.

10. The composition according to any of claims 7 to 9, wherein the coating oil is a source of eicosapentaenoic acid ("EPA") and/or docosahexaenoic acid ("DHA").

11. The composition according to claim 1, wherein the composition is an aquaculture feed and preferably a fish feed pellet and wherein the feed comprises at least one additional component, wherein
 a. the additional component is 25-55% (w/w) of a protein source, or
 b. the additional component is 10-25% (w/w) of a carbohydrate source, or
 c. the additional component is 15-40% (w/w) of a lipid source.

12. The composition according to claim 11, wherein the feed composition further comprises one or more ingredients selected from the group consisting of fish meal, krill meal, soya concentrate, corn gluten, wheat gluten, pea protein, wheat flour, fish oil, a vitamin, mineral premix, mineral premix plus synthetic phosphorus and combinations thereof.

13. The composition according to claim 11 or 12, wherein the feed pellet is an extruded feed pellet or a pressed feed pellet.

14. The composition according to any of claims 11 to 13, wherein the feed pellet is a coated feed pellet.

15. The composition according to any of claims 11 to 14, wherein the active ingredient is present in the coating of the coated feed pellet.

16. The composition according to any of claims 11 to 15, wherein the coating comprises an oil and alpha-lipolic acid.

17. The composition according to claim 16, wherein the amount of alpha-lipolic acid, a salt or derivative thereof present in the coating constitutes 100% by weight of the total alpha-lipolic acid, a salt or derivative thereof of the pellet.

18. A method of providing an extruded feed pellet, said method comprising the steps of:
 a) grinding and/or mixing of at least a carbohydrate source, a protein source, a lipid source, ash, water and optionally one more ingredients selected from the group consisting of fish meal, krill meal, soya concentrate, corn gluten, wheat gluten, pea protein, wheat flour, fish oil, a vitamin, mineral premix, mineral premix plus synthetic phosphorus and combinations thereof into a powder mixture,
 b) homogenizing the mixture in (a) until a paste is formed;
 c) extruding the paste obtained in step (b) by an extrusion installation comprising a mold and a number of mixing and kneading zones, composed of a plurality of alternately forward and backward kneading screw elements;
 d) cutting of the extruded material into porous pellets of a suitable length when it exits the die;
 e) drying of the porous pellets;
 f) adding a composition with a coating oil according to any of claims 7 to 10 to the pellets obtained in step (e) and adsorbing said oil into the porous pellet under vacuum, and
 g) cooling of the pellets, and
 h) obtaining a coated fish feed pellet.

19. Use of alpha-lipoic acid, a salt or derivative thereof for improving the feed conversion ratio and/or the standard growth rate in aquatic animals.

20. Use of alpha-lipoic acid, a salt or derivative thereof for reducing mortality in aquatic animals.

21. Use of alpha-lipoic acid, a salt or derivative thereof for the treatment and/or prevention of diseases caused by pathogenic microorganisms or viruses in aquatic animals.

22. A method for improving the feed conversion ratio and/or the standard growth rate in aquatic animals, said method comprises feeding to the aquatic animal a feed comprising alpha-lipoic acid, a salt or derivative thereof.

23. A method for reducing mortality in aquatic animals, said method comprises feeding to the aquatic animal a feed comprising alpha-lipoic acid, a salt or derivative thereof.

24. A method for the treatment and/or prevention of diseases caused by pathogenic microorganisms or viruses in aquatic animals, said method comprises feeding to the aquatic animal a feed comprising alpha-lipoic acid, a salt or derivative thereof.

25. A composition comprising alpha-lipoic acid, a salt or derivative thereof for use in improving the feed conversion ratio and/or the standard growth rate in aquatic animals.

26. A composition comprising alpha-lipoic acid, a salt or derivative thereof for use in reducing mortality in aquatic animals.

27. A composition comprising alpha-lipoic acid, a salt or derivative thereof for use in the treatment and/or prevention of diseases caused by pathogenic microorganisms or viruses in aquatic animals.

28. The composition or feed according to claims 24 or 27, wherein the disease is pancreatic disease.

29. The composition according to claim 28, wherein the virus is an alpha virus (SAV), Noda virus (VNN), white spot syndrome virus (WSSV).

30. The composition according to claim 29, wherein the alpha virus is salmonid alpha-virus subtype 3 (SAV-3) virus.

31. The composition according to any of claims 25 to 30, wherein said composition comprises alpha-lipoic acid, a salt or derivative thereof in an amount of at least 150-1000 mg per kg feed.

32. The composition according to any of claims 25 to 30, wherein said composition comprises alpha lipolic acid, a salt or derivative thereof in an amount of at least 150, 200, 250, 300, 350, 400, 450, 500, 550, 600, 650, 700, 750, 800, 850, 900, 950, 1000 mg per kg feed.

33. The composition according to any of claims 25 to 30, wherein said composition comprises alpha lipolic acid, a salt or derivative thereof in an amount of 150-1000, 200-1000, 250-1000, 300-1000, 350-1000, 400-1000, 450-1000 500-1000, 550-1000, 600-1000, 650-1000, 700-1000, 750-1000, 800-1000, 850-1000, 900-1000, or 950-1000 mg per kg feed.

34. The composition according to any of claims 25 to 33, wherein said composition is administered to an aquatic animal of the group consisting of salmon, trout, bream, bass and decapod crustacean.

35. The composition according to any of claims 25 to 33, wherein said composition is administered to the salmon, trout, bream and/or bass in the fresh water (FW) phase.

36. The composition according to any of claims 25 to 33, wherein said composition is administered to the salmon, trout, bream and/or bass in the sea water (SW) phase.

37. The composition according to any of claims 25 to 36, wherein said composition is administered to the salmon, trout, bream and/or bass in the period after hatching and until slaughter.

38. The composition according to any of claims 34 to 37, wherein the salmon is of the family Salmonidae.

39. The composition according to any of claims 34 to 38, wherein the salmon is selected from the group consisting of the genus *Salmo, Oncorhynchus* and *Salvenis*.

40. The composition according to any of claims 34 to 38, wherein the aquatic animal of the genus *Salmo* is selected from the group consisting of Atlantic salmon (*Salmo salar*) and Brown trout (*Salmo trutta*).

41. The composition according to any of claims 39 or 40, wherein the aquatic animal of the genus *Oncorhynchus* is selected from the group consisting of Chinook salmon (*Oncorhynchus tshawytsch*), Rainbow trout (*Oncorhynchus mykiss*), Sockeye salmon (*Oncorhynchus nerka*) and Coho salmon (*Oncorhynchus kisutch*).

42. The composition according to any of claims 39 or 40, wherein the aquatic animal of the genus *Salvenis* is selected from the group consisting of Arctic charr (*Salvelinus alpinus*), Brook trout (*Salvelinus fontinalis*) and Lake trout (*Salvelinus namaycush*).

43. The composition according to any of claims 34 to 42, wherein the aquatic animal is selected from the group consisting of Atlantic salmon (*Salmo salar*), Brown trout (*Salmo trutta*) and Rainbow trout.

44. The composition according to any of claims 34 to 42, wherein the aquatic animal is a fish selected from the group consisting of fry, fingerlings, parr, smolts and adult fish.

EXAMPLE

Example 1: Preparation of Pressed Fish Feed

The main raw materials are ground and mixed. Microingredients are then added to the mixer and the homogenous mix is conditioned by adding water and steam to the mass in a preconditioner. This starts a cooking process in the starch fraction (the binding component). The mass is fed into a pellet mill. The mass is forced through the mill's die and the strings are broken into pellets on the outside of the die. The moisture content is low and drying of the feed is not necessary.

Additional oil including a fish feed composition according to the present invention is then sprayed onto the surface of pellets, but as the pellets are rather compact, the total lipid content rarely exceeds 24%. The added oil may be fish oil, microbial/algal or vegetable oils, for example rape seed oil or soy oil, or a mixture of oils. After oil coating, the pellets are cooled in a cooler and bagged. The final pressed fish feed contains 10 to 5000 ppm of the composition as described in the invention.

Example 2: Method for Preparation of Extruded Fish Feed

The main raw materials are ground and mixed. Micro ingredients incl. a fish feed composition according to the invention are added to the mixer. The homogenous mix is conditioned by adding water and steam to the mass in a preconditioner.

Additional oil may also be added to the mass at this stage. This starts a cooking process in the starch fraction (the binding component). The mass is fed into an extruder. The extruder may be of the single screw or the twin-screw type. Due to the rotational movement of the mass in the extruder, the mass is further mixed. Additional oil, water and steam may be added to the mass in the extruder. At the end of the extruder, the mass has a temperature above 100° C. and a pressure above ambient pressure. The mass is forced through the openings in the extruder's die plate. Due to the relief in temperature and pressure, some of the moisture will evaporate immediately (flash off) and the extruded mass becomes porous. The strings are cut into pellets by a rotating knife. The water content is rather high (18-28%) and the pellets are therefore immediately dried to approximately 10% water content in a dryer.

After the dryer, more oil including a feed additive composition according to the invention may be added to the feed by spraying oil onto the surface of the feed, or by dipping the feed in oil. It is advantageous to add the oil to the feed in a closed vessel where the air pressure is below ambient (vacuum coating) so that the porous feed pellets absorb more oil. Feed containing more than 40% lipid may be produced this way. After the coater, the feed is cooled and bagged. Oil may be added at several places in the process as explained above, and may be fish oil, microbial/algal or vegetable oils, by example rape seed oil or soy oil, or a mixture of oils.

Fish need protein, fat, minerals and vitamins in order to grow and to be in good health. The diet of carnivorous fish is particularly important. Originally in the farming of carnivorous fish, whole fish or ground fish were used to meet the nutritional requirements of the farmed fish. Ground fish mixed with dry raw materials of various kinds, such as fish meal and starch, was termed soft or semi-moist feed. As farming became industrialized, soft or semi-moist feed was replaced by pressed dry feed. This was itself gradually replaced by extruded dry feed.

Today, extruded feed is nearly universal in the farming of a number of fish species such as various types of salmonid, cod, sea bass and sea bream.

The dominant protein source in dry feed for fish has been fish meal of different qualities. Other animal protein sources are also used for dry fish feed. Thus, it is known to use blood meal, bone meal, feather meal and other types of meal produced from other slaughterhouse waste, for example chicken meal. These are typically cheaper than fish meal and fish oil. However, in some geographic regions, there has been a prohibition against using such raw materials in the production of feeds for food-producing animals and fish.

It is also known to use vegetable protein such as wheat gluten, maize (corn) gluten, soya protein, lupin meal, pea meal, bean meal, rape meal, sunflower meal and rice flour.

Example 3: Method for Preparation of Alpha Lipoic Acid Composition in Oil

Alpha lipoic acid (AL) in the form of a powder is sieved through a 1 mm grid to remove larger particles. A small amount of oil is preheated to 45° C. and mixed with the powder to form a homogeneous liquid paste. The added oil may be fish oil, microbial/algal or vegetable oils, for example rape seed oil or soy oil, or a mixture of oils. More oil is added until the desired concentration is reached. The oil functions as a carrier. This AL composition can be sprayed while stirring to prevent the AL from settling. The composition is used to coat the feed described in examples 1 and 2.

Example 4—Study 1: Mortality in A. Salmon Fry Following SAV Challenge

The first study evaluated dietary alpha-lipoic acid (LA) at 500 mg/kg compared to control basal diet fed fish. Pre-feeding experimental diets for ~5 weeks, growing from ~0.2 g to ~0.5 g in 4 replicate tanks per diet. Water temperature at 12° C.±1° C. Min. 30 fish per diet (tank). Disease challenge by cohabitation with fish infected with Salmon Alfa Virus (SAV).

This was intended to transmit the infection to the test groups leading to clinical Pancreas Disease (PD). The challenge lasted for 9.5 weeks (~2 g), mortality recorded daily.

Significantly higher survival was observed for the lipoic acid fed fish, representing an improvement by 63% relative percent survival (RPS) compared to the control diet fed fish (FIG. 1).

FIG. 1. Accumulated mortality in A. salmon fry following SAV challenge comparing fish fed control diet or 500 mg/kg LA.

Example 5—Study 2: Mortality in A. Salmon Fry Following SAV Challenge 2

The second study evaluated dietary alpha-lipoic acid at 3 doses 125, 250 and 500 mg/kg compared to control basal diet fed fish for resistance to virus disease (PD). The experiment was carried out as described for the first study.

Figure 2:
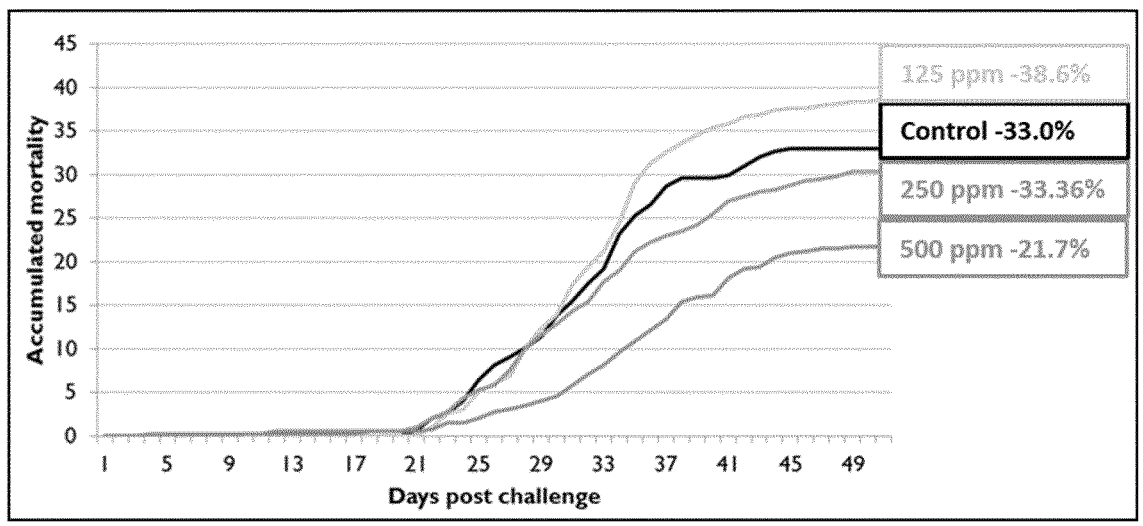
FIG. 2. Accumulated mortality in Atlantic salmon fry following SAV challenge evaluating for dose response of dietary alpha-lipolic acid.

As in the first study fish fed 500 mg/kg LA had significantly higher survival compared to the control diet fed fish (34% RPS, Table 1). At 250 mg/kg there was a tendency for improved survival but this was not statistically significant. There was no observed effect at the 125 mg/kg (FIG. 2).

TABLE 1

Relative Percent Survival (RPS) of A salmon fry after SAV challenge dependency on different diets

| Diets | RPS |
| --- | --- |
| Control vs. 125 ppm | −17% |
| Control vs. 250 ppm | 8% |
| Control vs. 500 ppm | 34% |

FIG. 2. Accumulated mortality in A. salmon fry following SAV challenge evaluating for dose response of dietary LA.

Example 6—Study 3: Mortality in A. Salmon Fry Following SAV Challenge 3

In this study three separate virus challenge trials evaluated dietary alpha-lipoic acid at 3 doses 250, 500 and 1000 mg/kg compared to control basal diet fed fish for resistance to virus disease (PD). The experiment was carried out as described for the first study.

Figure 3:
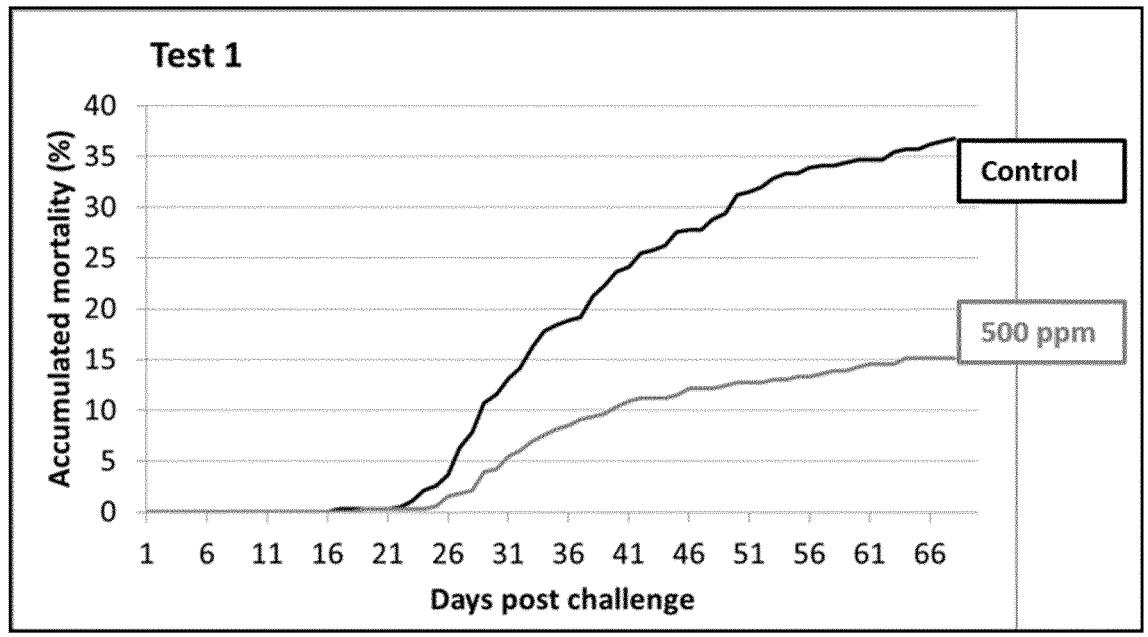
FIG. 3. Accumulated mortality in Atlantic salmon fry following SAV challenge evaluating for dose response of dietary alpha-lipolic acid. —Test 1
Figure 4:
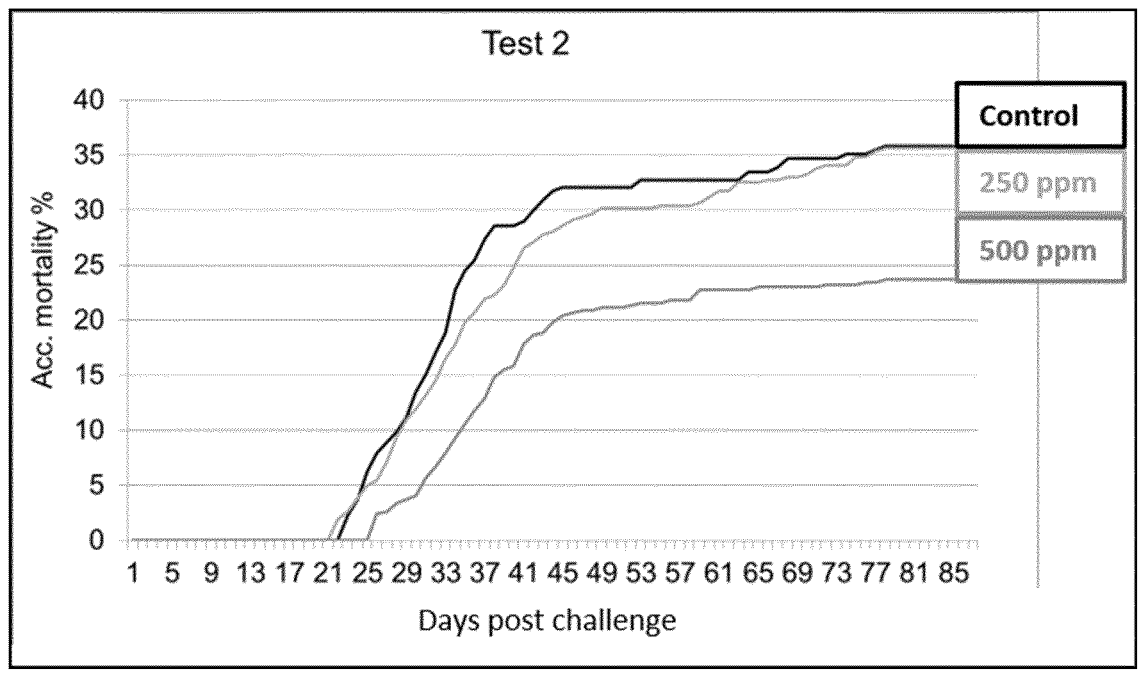
FIG. 4. Accumulated mortality in Atlantic salmon fry following SAV challenge evaluating for dose response of dietary alpha-lipolic acid. —Test 2
Figure 5:
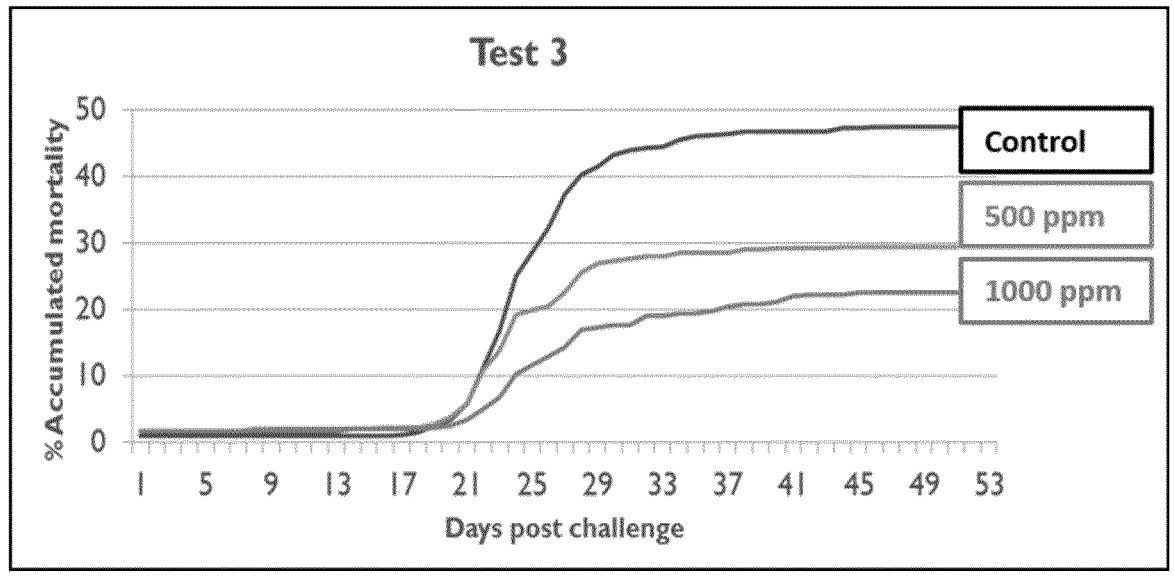
FIG. 5. Accumulated mortality in Atlantic salmon fry following SAV challenge evaluating for dose response of dietary alpha-lipolic acid. —Test 3

Showing significantly reduced end mortality with medium (500 mg/kg) and high dose (1000 mg/kg) of alpha lipoic acid additive in all trials (FIG. 3-5).

FIG. 3 Accumulated mortality in Atlantic salmon fry following SAV challenge evaluating for dose response of dietary alpha-lipolic acid. —Test 1

FIG. 4 Accumulated mortality in Atlantic salmon fry following SAV challenge evaluating for dose response of dietary alpha-lipolic acid. —Test 2

FIG. 5 Accumulated mortality in Atlantic salmon fry following SAV challenge evaluating for dose response of dietary alpha-lipolic acid. —Test 3

Example 7—Study 4: Mortality in A. Salmon Following IPN Challenge

The fourth study evaluated dietary alpha-lipoic acid at 3 doses 500, 750 and 1000 mg/kg compared to control basal diet fed fish for resistance to virus disease (IPN). The experiment was carried out as described for the first study.

Fish fed 750 mg/kg LA had significantly higher survival compared to the control diet fed fish (28% RPS). Fish fed 500 mg/kg LA also had significantly higher survival compared to the control diet fed fish (7% RPS). However, fish fed 1000 mg/kg LA had no significantly higher survival compared to the control diet fed fish (−1% RPS) (FIG. 3).

TABLE 2

Mean Survival, Mean Mortality and Relative Percent Survival (RPS) of A salmon after IPN challenge dependency on different diets

| | Control | 500 ppm | 750 ppm | 1000 ppm |
| --- | --- | --- | --- | --- |
| Mean Survival [%] | 59.1 | 62.0 | 70.4 | 58.7 |
| Mean mortality [%] | 40.9 | 38.0 | 29.6 | 41.3 |
| RPS [%] | | 7.1 | 27.6 | −1.0 |

Figure 6:
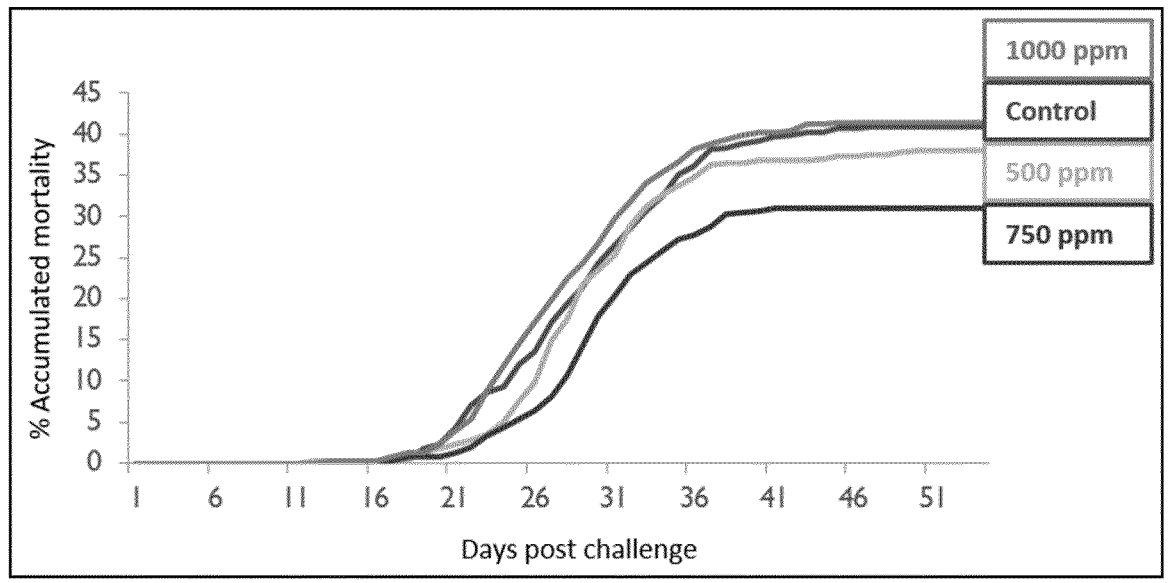
FIG. 6. Accumulated mortality in Atlantic salmon following IPN challenge comparing fish fed a control diet or a feed comprising 500, 750 and 1000 mg alpha-lipolic acid/kg feed.

FIG. 6. Accumulated mortality in Atlantic salmon following IPN challenge comparing fish fed control diet or a feed comprising 500, 750 and 1000 mg alpha-lipolic acid/kg feed.

Example 8—Study 5: Performance of Atlantic Salmon Following IPN Challenge

This study evaluated dietary alpha-lipoic acid at 3 doses 500, 750 and 1000 mg/kg compared to control basal diet fed fish for performance after disease (IPN) challenge in atlantic salmon and was carried out in succession of the fifth study by weighting the fish and comparing the challenged LA and control fed fish with the unchallenged control fed fish.

Performance in challenged fish was reduced compared to unchallenged fish. However, challenged fish fed 750 mg/kg LA had significantly better performance compared to the challenged control diet fed fish. Challenged fish fed 500 mg/kg LA also performed better compared to the challenged control diet fed fish. However, challenged fish fed 1000 mg/kg LA did not perform significantly better compared to the challenged control diet fed fish (FIG. 7).

Figure 7:
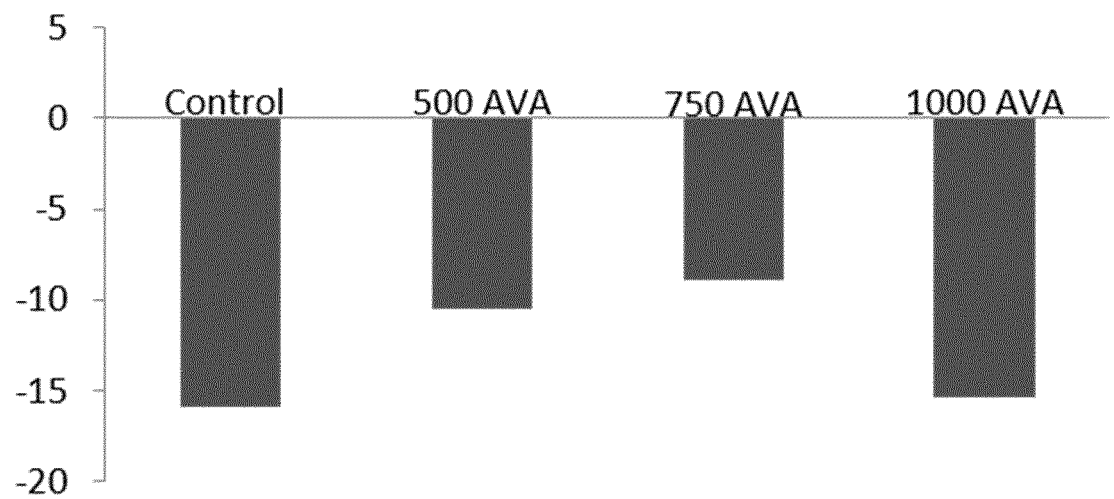
FIG. 7. Performance of Atlantic salmon following IPN challenge comparing growth reduction of challenged fish fed a control diet or a feed comprising 500, 750 and 1000 mg alpha-lipolic acid/kg feed with unchallenged control.

FIG. 7. Performance of Atlantic salmon following IPN challenge comparing growth reduction of challenged fish fed control diet or a feed comprising 500, 750 and 1000 mg alpha-lipolic acid/kg feed with unchallenged control.

Example 9—Study 6: Immune Response in RB Trout

Rainbow trout were fed for 4 weeks with graded levels of LA (125, 250 and 500 mg/kg) compared to basal control diet fed fish. A range of functional immune assays of tissues/cells obtained at the end of the feeding period were conducted to investigate the possible mode of action observed in the disease challenge studies.

The capacity of Oxidative burst of phagocytes was assayed to assess anti-oxidation or pro-oxidation activity, as widely reported for use of LA (Kutter et al., 2014). There was no significant difference in extracellular or intracellular oxidative burst for any of the treatment groups indicating that the mechanism was not due to oxidation biochemical pathways (FIG. 4).

Figure 8:
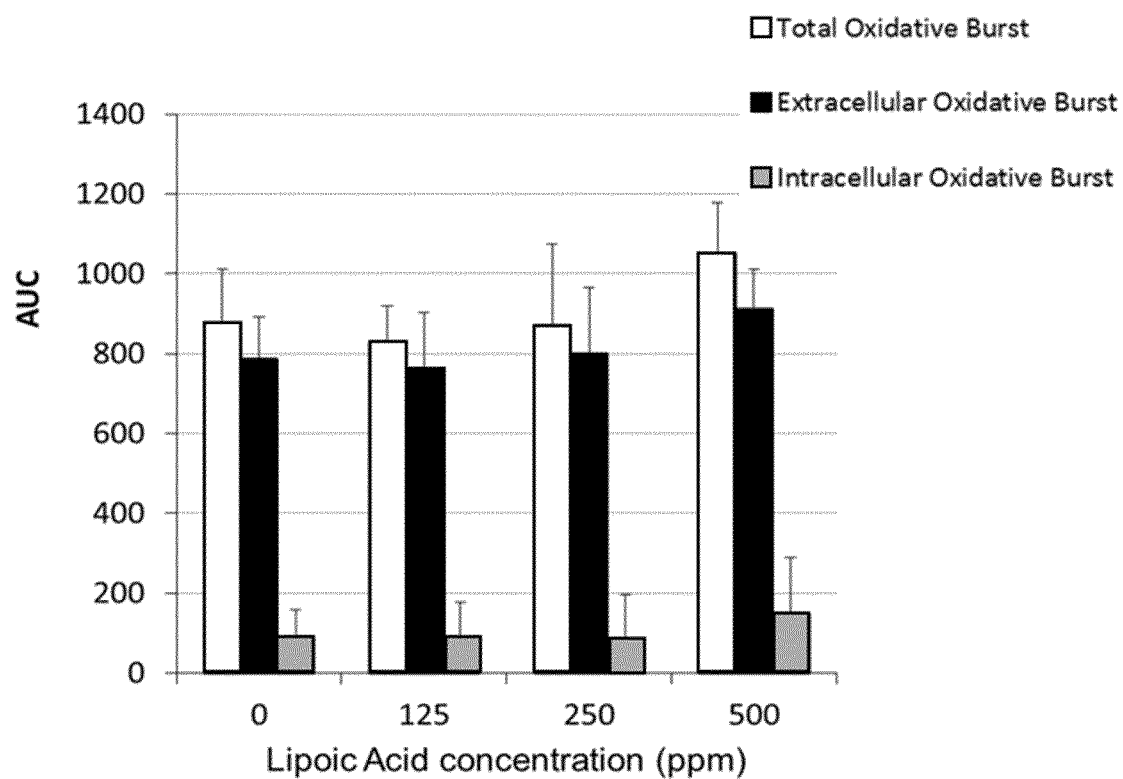
FIG. 8. Oxidative burst of phagocytes in rainbow trout fed graded levels of dietary alpha-lipolic acid for 4 weeks.

FIG. 8. Oxidative burst of phagocytes in rainbow trout fed graded levels of dietary LA for 4 weeks.

The apoptosis pathway (programmed cell death) was investigated by assaying the ability of lymphocytes to prevent apoptosis occurring following incubation with Campto, a chemical stimulator of apoptosis. There was a clear dose response of dietary LA for reduction of apoptotic cells with a significant reduction in lymphocytes from fish fed 500 mg/kg LA. This level of reduction in apoptosis is quite remarkable. There was also a trend for lower basal apoptosis activity where no Campto was used in LA treatment groups (not significant) (FIG. 5).

Figure 9:
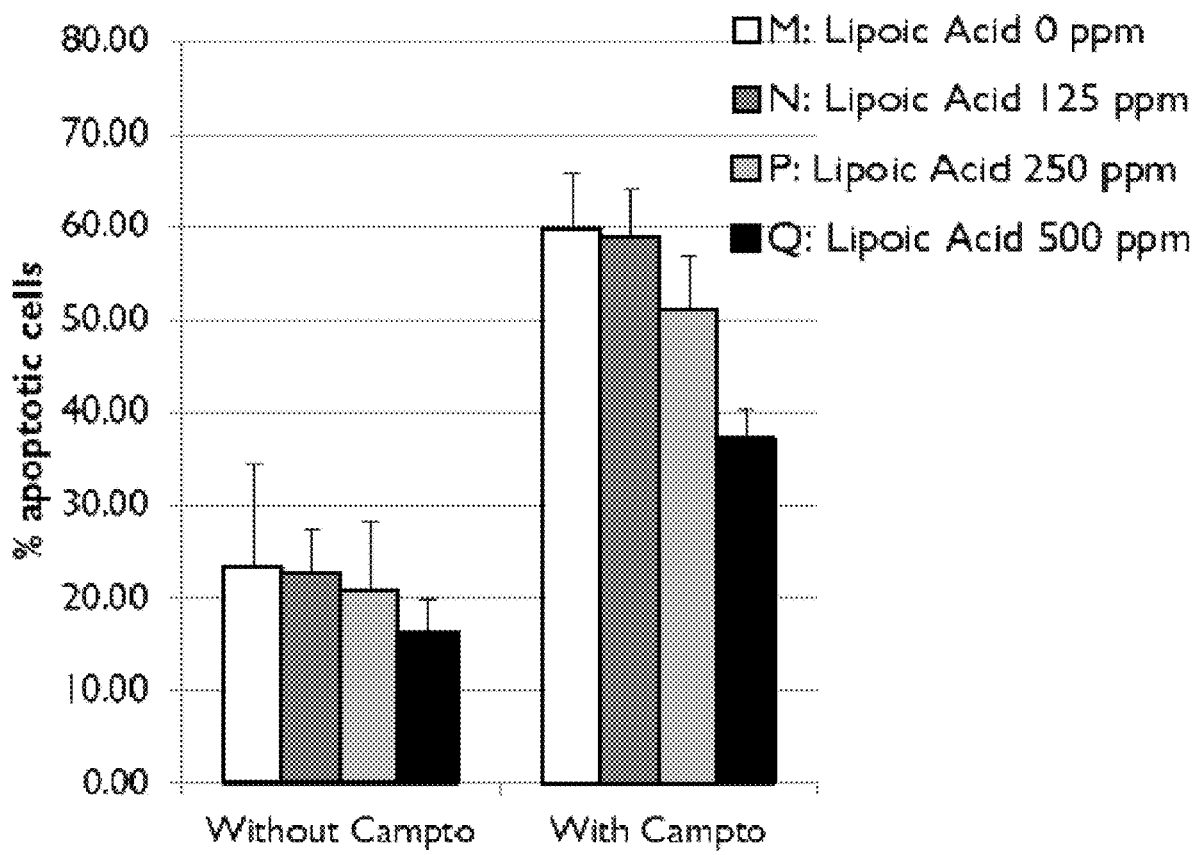
FIG. 9. Apoptosis of lymphocytes in rainbow trout fed graded levels of dietary alpha-lipolic acid for 4 weeks.

FIG. 9. Apoptosis of lymphocytes in rainbow trout fed graded levels of dietary LA for 4 weeks.

Example 10—Study 7: FCR in RB Trout

This study evaluated dietary alpha-lipoic acid at 3 doses 250, 500 and 1000 mg/kg compared to control basal diet fed fish for feed conversion ratio. Rainbow trout with an initial weight around 50 g were fed for ~6 weeks with graded levels of LA compared to basal control diet fed fish in 4 replicate tanks per diet with 50 fish per tank. The fish were fed automatically and daily with an excess of experimental diets with regard to feeding instructions for control basal diet and weighted every two weeks. Excess feed was removed daily.

In this study fish fed LA showed improved feed conversion ratios compared to the control diet fed fish (FIG. 6).

TABLE 3

(Cumulative) Feed conversion ratio (FCR) in rainbow trout dependency on different diets

| IMS182 | Feed as fed basis (kg)/weight gain (kg) | | | |
| --- | --- | --- | --- | --- |
| Period (days) | Mean Ctrl | Mean AL 250 | Mean AL 500 | Mean AL 1000 |
| 0-15 | 0.68 | 0.65 | 0.66 | 0.65 |
| 0-30 | 0.69 | 0.67 | 0.67 | 0.67 |
| 0-44 | 0.68 | 0.67 | 0.68 | 0.68 |

Figure 10:
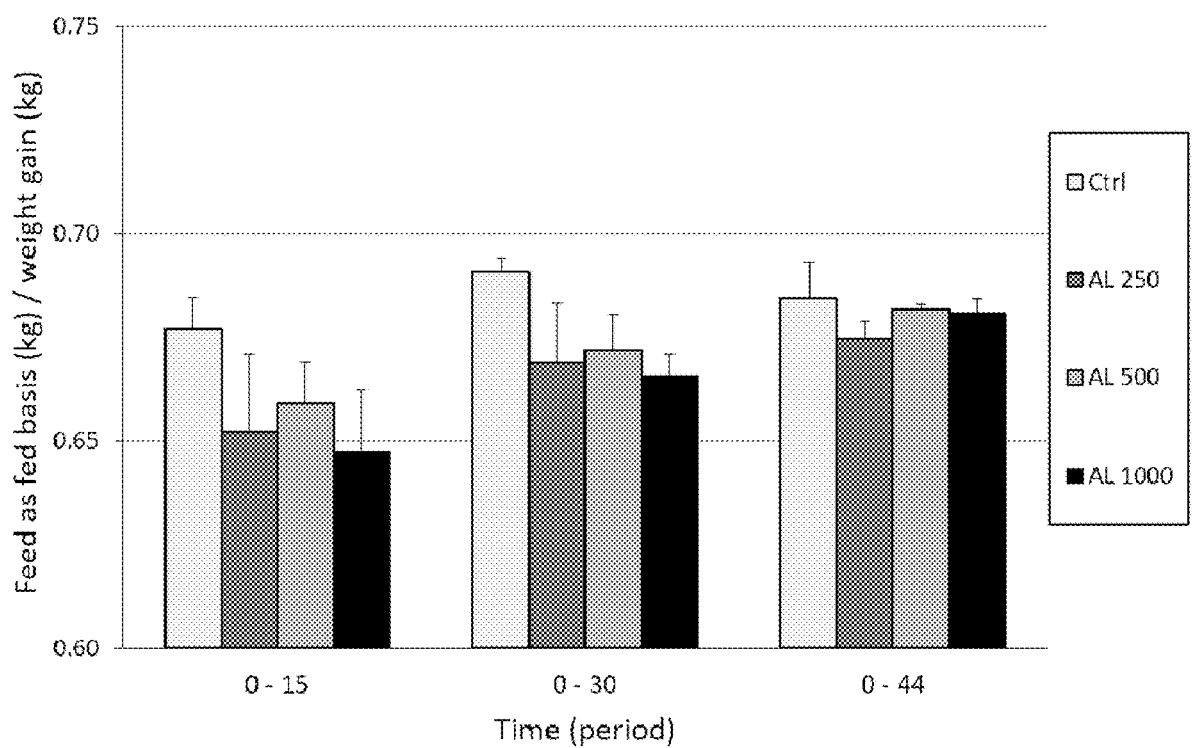
FIG. 10. Cumulative feed conversion ratio (FCR) in rainbow trout fed graded levels of dietary alpha-lipolic acid for 41 days.

FIG. 10. (Cumulative) Feed conversion ratio (FCR) in rainbow trout fed graded levels of dietary alpha-lipolic acid for 41 days.

Example 11—Study 8: Mortality in Sea Bass Fry Following VNN (Noda Virus) Challenge The seventh study evaluated dietary alpha-lipoic acid (LA) at 250, 500 and 750 mg/kg compared to control basal diet fed fish in Sea Bass fry. Pre-feeding experimental diets for 5-6 weeks, growing from ~0.7 g to ~1.4 g. Water temperature at 25° C. 133 fish per diet (tank). Disease challenge by cohabitation with fish infected with Noda Virus (VNN). This was intended to transmit the infection to the test groups. Mortality was recorded daily.

Significantly higher survival was observed for the 500 mg/kg lipoic acid fed fish, representing an improvement by 66% relative percent survival (RPS) compared to the control diet fed fish. Significantly higher survival was also observed for the 250 and 750 mg/kg lipoic acid fed fish, representing an improvement by 60 and 45% relative percent survival (RPS) compared to the control diet fed fish (FIG. 8).

Figure 11:
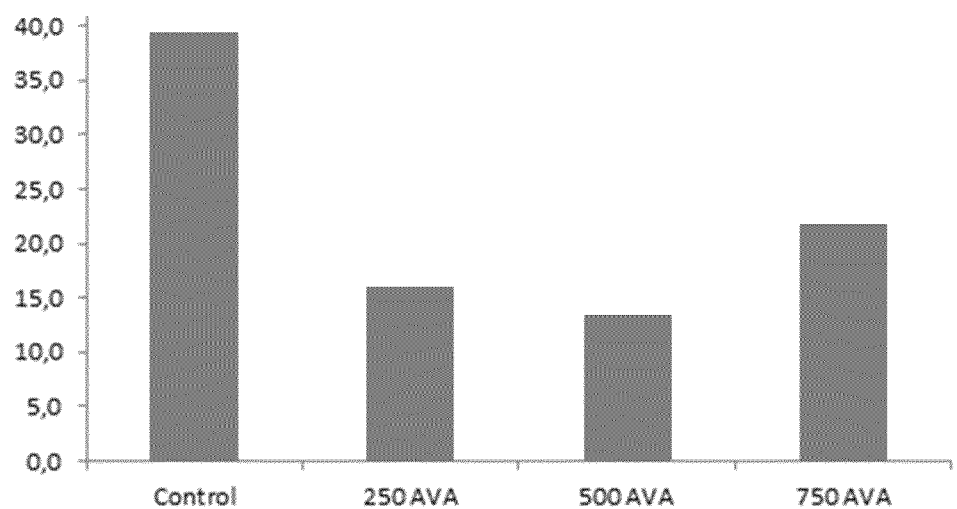
FIG. 11. Accumulated mortality in Sea Bass fry following VNN (Nods virus) challenge comparing fish fed a control diet or a feed comprising 250, 500 and 750 mg alpha-lipolic acid/kg feed.

FIG. 11. Accumulated mortality in Sea Bass fry following VNN (Noda virus) challenge comparing fish fed control diet or a feed comprising 250, 500 and 750 mg alpha-lipolic acid/kg feed.

TABLE 4

Mean Survival, Mean Mortality and Relative Percent Survival (RPS) of Sea Bass fry after VNN challenge dependency on different diets

| | control | 250 ppm | 500 ppm | 750 ppm |
| --- | --- | --- | --- | --- |
| Mean Survival [%] | 60.8 | 84.2 | 86.7 | 78.3 |
| Mean Mortality [%] | 39.2 | 15.8 | 13.3 | 21.7 |
| RPS [%] | 0.0 | 59.6 | 66.0 | 44.7 |

Example 12—Study 9: Mortality in Shrimp Following WSSV Challenge

The fourth study evaluated dietary alpha-lipoic acid at 650 mg/kg compared to control basal diet fed shrimp for resistance to white spot syndrome virus disease (WSSV). The experiment was carried out under standard conditions for shrimp. Pre-feeding experimental diets for ~4 weeks. Mortality was recorded daily.

Shrimp fed 650 mg/kg LA had higher survival compared to the control diet fed shrimp (8.7% RPS, Table 5).

TABLE 5

Mean Survival, Mean Mortality and Relative Percent Survival (RPS) of shrimp after WSSV challenge dependency on different diets

| | Control | 650 ppm |
| --- | --- | --- |
| Mean Survival [%] | 23.3 | 30.0 |
| Mean mortality [%] | 76.7 | 70.0 |
| RPS [%] | | 8.7 |

The invention claimed is:

1. A coated feed pellet for intake by an aquatic animal, wherein the coated feed pellet comprises:
    (a) an aquatic feed pellet formed of a feed additive composition comprising aquatic animal feed ingredients, and
    (b) a coating on the aquatic feed pellet, wherein the coating comprises:
        (b1) a carrier oil coating the aquatic feed pellet, and
        (b2) an alpha-lipoic acid, a salt or derivative thereof as an active ingredient in the form of a powder having a particle size below 1 mm which is embedded in the carrier oil, wherein
    the carrier oil is at least one oil selected from the group consisting of fish oils, microbial oils and vegetable oils, and wherein
    the active ingredient is present in a final feed administered to the aquatic animal in a concentration within a range of from 100-500 mg per kg feed.

2. The coated feed pellet according to claim 1, wherein the feed additive composition is a feed premix, and wherein the feed premix further comprises at least one additional component selected from the group consisting of fat-soluble vitamins, water soluble vitamins, trace minerals, carotenoids, polyunsaturated fatty acids, probiotics, prebiotics and macro minerals.

3. The coated feed pellet according to claim 2, wherein the fat-soluble vitamin is vitamin E.

4. The coated feed pellet according to claim 2, wherein the fat-soluble vitamin is at least one compound selected from the group consisting of alpha-tocopherol, beta-tocopherol, gamma-tocopherol, delta-tocopherol, alpha-tocotrienol, beta-tocotrienol, gamma-tocotrienol, delta-tocotrienol and esters thereof.

5. The coated feed pellet according to claim 1, wherein said coating oil comprises oleic acid (18:1 n-9) in the range 0.28-229.15 g/kg feed, linoleic acid in the range 0.22-233.24 g/kg feed, alfa-linolenic acid in the range 0.28-225.06 g/kg, arachidonic acid (ARA, 20:4 n-6) in the range 0.03-24.55 g/kg, eicosapentaenoic acid (EPA, 20:5 n-3) in the range 0.03-73.66 g/kg and docosahexaenoic acid (DHA, 22:6 n-3) in the range 0.03-73.66 g/kg.

6. The coated feed pellet according to claim 5, wherein the vegetable oil is selected from the group consisting of rape seed oil, soy oil and camelina oil.

7. The coated feed pellet according to claim 1, wherein the coating oil is a source of eicosapentaenoic acid ("EPA") and/or docosahexaenoic acid ("DHA").

8. The coated feed pellet according to claim 1, wherein the composition is an aquaculture feed, and wherein the aquatic animal is a salmon, and wherein the feed additive composition further comprises: at least one additional component, wherein the at least one additional component is either:

(a1) 25-55% (w/w) of a protein source,
(a2) 10-25% (w/w) of a carbohydrate source, or
(a3) 15-40% (w/w) of a lipid source.

9. The coated feed pellet according to claim 8, wherein the feed composition further comprises one or more ingredients selected from the group consisting of fish meal, krill meal, soya concentrate, corn gluten, wheat gluten, pea protein, wheat flour, fish oil, a vitamin, mineral premix, mineral premix plus synthetic phosphorus and combinations thereof.

10. The coated feed pellet according to claim 1, wherein the aquatic feed pellet is an extruded aquatic feed pellet or a pressed aquatic feed pellet.

11. The coated feed pellet according to claim 10, wherein the amount of alpha-lipolic acid, a salt or derivative thereof present in the coating constitutes 100% by weight of the total alpha-lipolic acid, a salt or derivative thereof of the coated feed pellet.

* * * * *